US00RE38792E

(19) United States
(12) Reissued Patent
Ishihara et al.

(10) Patent Number: US RE38,792 E
(45) **Date of Reissued Patent: *Sep. 6, 2005**

(54) MODIFIED BACTERIAL CELLULOSE

(75) Inventors: Masaru Ishihara, Kawasaki (JP); Shigeru Yamanaka, Kawasaki (JP)

(73) Assignee: Ajinomoto Co., Ltd., Tokyo (JP)

( * ) Notice: This patent is subject to a terminal disclaimer.

(21) Appl. No.: 10/140,040

(22) Filed: May 8, 2002

Related U.S. Patent Documents

Reissue of:
(64) Patent No.: 6,060,289
Issued: May 9, 2000
Appl. No.: 08/900,124
Filed: Jul. 25, 1997

(30) Foreign Application Priority Data

Jul. 26, 1996 (JP) ..... 8-215332
Feb. 28, 1997 (JP) ..... 9-062282

(51) Int. Cl.[7] ..... C12P 19/04
(52) U.S. Cl. ..... 435/101; 536/56; 536/126; 536/123.12
(58) Field of Search ..... 435/101; 536/56, 536/126, 123.12

(56) References Cited

U.S. PATENT DOCUMENTS 4,742,164 A 5/1988 Iguchi et al.
4,745,058 A 5/1988 Townsley et al.
4,863,565 A 9/1989 Johnson et al.
6,060,289 A 5/2000 Ishihara et al.
6,627,419 B2 * 9/2003 Ishihara et al. ..... 435/101

FOREIGN PATENT DOCUMENTS

JP 7-79791 3/1995

OTHER PUBLICATIONS

Chemical Abstracts, vol. 122, No. 25, Jun. 19, 1995, 313074v, Food gel manufacture with acetic acid bacteria in the presence of oxidoreduction adjusting agents, p. 804.
S. Hestrin et al, Nature, Jan. 11, 1947, vol. 159, Synthesis of Cellulose by Resing Cells of *Acetobacter xylinum*, pp. 64–65.

* cited by examiner

*Primary Examiner*—Francisco Prats
(74) *Attorney, Agent, or Firm*—Oblon, Spivak, McClelland, Maier & Neustadt, P.C.

(57) ABSTRACT

[This invention provides a bacterial cellulose comprising ribbon-shaped microfibrils having a thickness of 10 to 100 nm and a width of 160 to 1000 nm or a bacterial cellulose comprising ribbon-shaped microfibrils having a thickness of 10 to 100 nm and a width of 50 to 70 nm. The former bacterial cellulose can be produced by culturing cellulose-producing bacteria in a culture medium containing a cell division inhibitor, and the latter can be produced by culturing the bacterium in a culture medium containing an organic reducing agent. The bacterial cellulose is modified from conventional bacterial cellulose in the major axis, and is improved in Young's modulus, etc.] *This invention provides a bacterial cellulose comprising ribbon-shaped microfibrils having a thickness of 1 to 9 nm and a width of 160 to 1000 nm or a bacterial cellulose comprising ribbon-shaped microfibrils having a thickness of 1 to 9 nm and a width of 50 to 70 nm. The former bacterial cellulose can be produced by culturing cellulose-producing bacteria in a culture medium containing a cell division inhibitor, and the latter can be produced by culturing the bacterium in a culture medium containing an organic reducing agent. The bacterial cellulose is modified from conventional bacterial cellulose in the major axis, and is improved in Young's modulus, etc.*

42 Claims, 5 Drawing Sheets

| | DISTANCE [nm] | DIFFERENCE IN HEIGHT [nm] | ANGLE [°] |
|---|---|---|---|
| — | 86.54 | 13.91 | 4.57 |

| | DISTANCE [nm] | DIFFERENCE IN HEIGHT [nm] | ANGLE [°] |
|---|---|---|---|
| — | 123.25 | 21.24 | 4.89 |

MODIFIED BACTERIAL CELLULOSE

Matter enclosed in heavy brackets [ ] appears in the original patent but forms no part of this reissue specification; matter printed in italics indicates the additions made by reissue.

BACKGROUND OF THE INVENTION

This invention relates to bacterial cellulose (BC) of which ribbon-shaped microfibrils are artificially modified to improve Young's modulus and a method of producing the same.

The bacterial cellulose can be used as various industrial materials, clothing materials, materials for medical supplies, functional materials, materials for foods and so on.

It is known that Acetobacter xylinum ATCC 23769 produces a mat-shaped cellulose which can be used for medical pads (Japanese Patent KOKAI 59-120159). It is also known that Acetobacter aceti subsp. xylinum ATCC 10821, etc. produce bacterial cellulose composed of ribbon-shaped microfibrils (U.S. Pat. No. 4,742,164). The size of the ribbon-shaped microfibrils is said to be 20 to 50 nm (Ed. by Tokyo Techno. Forum Secretariat, "Jinrui to Bio (Humanity and Bio)", P329, 1993 Yomiuri Nippon Television (enter) which may be measured without discrimination of the major axis (width and the minor axis (thickness).

The bacterial cellulose is produced as floc or suspended matter in a form of sheet, dispersion, grain or the like by static culture or aeration agitation culture which effects entangling of fibers. However, although the above macroscopic variation occurs, ribbon-shaped microfibril and properties of the bacterial cellulose are substantially not varied.

Structure and properties of bacterial cellulose are slightly different according to the type of bacterium. However it has not been reported to produce modified bacterial cellulose by changing the form of cellulose-producing bacteria artificially to vary ribbon-shaped microfibrils.

SUMMARY OF THE INVENTION

An object of the invention is to develop a bacterial cellulose, wherein the major axis (width) of ribbon-shaped microfibril is varied, and various properties, especially Young's modulas are improved.

The inventors investigated in order to achieve the above object, and found that a modified bacterial cellulose wherein ribbon-shaped microfibrils are varied can be obtained by adding a cell division inhibitor or an organic reducing agent to a culture medium which induces variation of the shape of cellulose - producing bacteria, and that properties, especially Young's modulus, are improved compared with conventional bacterial cellulose.

Thus, the present invention provides, bacterial cellulose comprising ribbon-shaped microfibrils having a thickness of [10 to 100] *1 to 9* nm and a width of 160 to 1000 nm, a method of producing bacterial cellulose which comprises culturing cellulose-producing bacteria which produce the bacterial cellulose extracellularly in a culture medium containing a cell division inhibitor, and recovering the bacterial cellulose produced in the culture medium, and further the present invention provides bacterial cellulose comprising ribbon-shaped microfibrils having a thickness of [10 to 100] *1 to 9* nm and a width of 50 to 70 nm, and a method of producing bacterial cellulose which comprises culturing cellulose-producing bacteria which produce the bacterial cellulose extracellularly in a culture medium containing an organic reducing agent, and recovering the bacterial cellulose produced in the culture medium.

In the invention, a section of a ribbon-shaped microfibril perpendicular to the growth direction (lengthwise direction) is assumed a rectangle, and one side is called the width or the major axis and the other side is called the thickness or the minor axis. In general, the length of the major axis is longer than the minor axis.

The microfibril of bacterial cellulose of the invention can be discriminated from conventional microfibrils by measuring the length of each major axis and minor axis using an electron microscope of atomic force microscope.

It is seemed that the shape or the number of cellulose secretion port varies due to the variation of the shape of the bacterium, and thereby, the shape of microfibril is varied. From experimental results, bacterial cellulose produced by long cell bacteria has a higher clarity than short cell bacteria, and the results suggest that the cellulose produced by long cell bacteria is in a more dense state. This is also supported by the observation of bacterial cellulose using a scanning electron microscope (SEM) and an atomic force microscope, and therefore, the cellulose produced by long cell bacteria has a more dense layer structure. In the conventional cellulose produced by normal bacteria, portions where cellulose is deposited in a helicoidal (cholesteric) form are observed, but the portions are not present in the cellulose produced by long cell bacteria. As to crystal width, it is considered that the cellulose produced by long cell bacteria is, although slightly, greater than the cellulose produced by normal bacteria in all lattice planes. In all bacterial cellulose, 0.6 nm lattice planes are oriented against film face, the cells are greater, the orientation degree is higher. In the observation of bacterial celluloses using a transmission electron microscope (TEM), the width of ribbon-shaped microfibril produced by long cell bacteria is greater than that produced by normal bacteria.

DETAILED DESCRIPTION OF THE INVENTION

Figure 1:
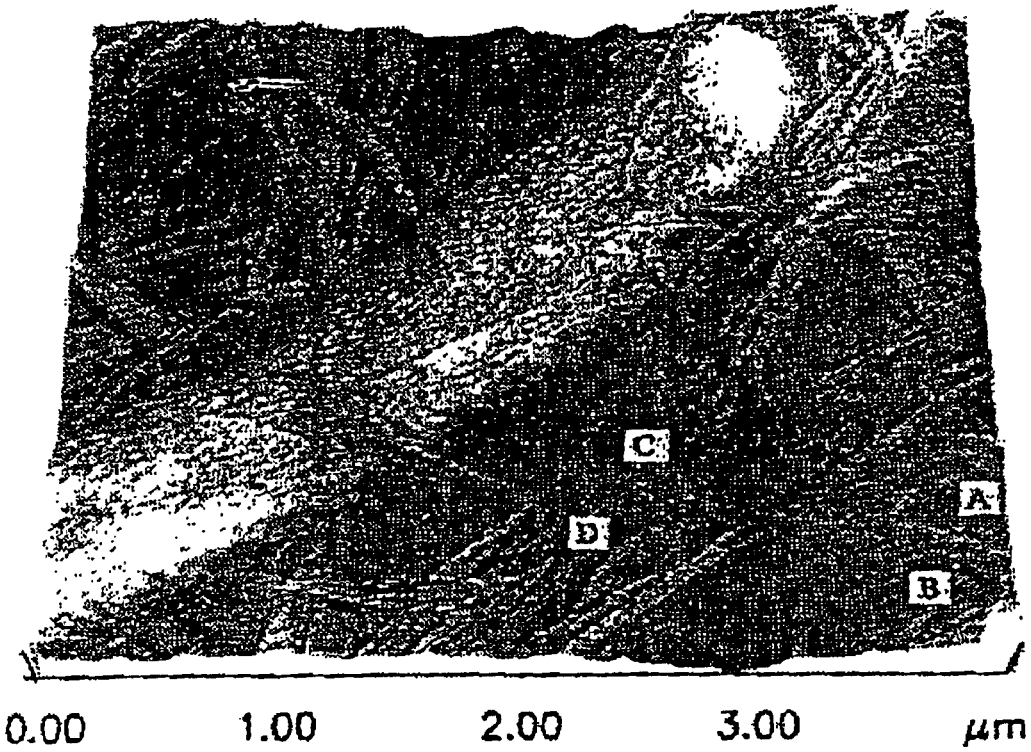
FIG. 1 is a photograph of an atomic force microscope showing a shaped of cellulose fiber and a cellulose-producing bacterium which was cultured without cell division inhibitor and organic reducing agent.

The bacterial cellulose of the invention comprises ribbon-shaped microfibrils having a minor axis of [10 to 100] *1 to*

9 nm and a major axis of 160 to 1000 nm or 50 to 70 nm. The inventors cultured cellulose producing bacteria (Acetobacter pasteurianus FERM BP-4176) in a culture medium without containing cell division inhibitor and organic reducing agent, and the size of the microfibrils of the bacterial cellulose was measured. As a result, the microfibril had a minor axis of [10 to 100] *1 to 9* nm and a major axis of 80 to 150 nm. Accordingly, the bacterial cellulose of the invention is clearly different from conventional bacterial cellulose.

The minor axis of microfibrils is[, in general, 55 to 95 nm, occasionally smaller size, e.g., 25 nm,] *1 to 9 nm* irrespective of the bacterial cellulose of the invention obtained by culturing in a culture medium containing a cell division inhibitor or an organic reducing agent or conventional bacterial cellulose obtained by culturing in a culture medium not containing cell division inhibitor and organic reducing agent.

On the other hand, the major axis of the microfibrils of the bacterial cellulose obtained by culturing in a culture medium containing a cell division inhibitor is, in general, 160 to 700 nm, particularly 170 to 600 nm, occasionally longer size, e.g.1000 nm. That is, the major axis is considerably greater compared with conventional major axis of 80 to 150 nm. When a culture medium contains a cell division inhibitor, cellulose-producing bacteria are lengthened, and it is observed that a plurality of single chains are adhered to each other to form a bundle. The bundle can be deemed single chain, and accordingly, the major axis becomes considerably longer than conventional one. The ratio of major axis:minor axis is about [2.8:1.0 or 8.1:1.0] *28:1 to 1000:1*, particularly, [3.0:1.0 to 6.0:1.0. In the case of conventional microfibrils, the ratio of major axis/minor axis is 1.6:1.0 to 2.7:1.0] *28:1.0 to 280:1*.

In the case of the bacterial cellulose obtained by culturing in a culture medium containing an organic reducing agent, the major axis of the microfibrils is, in general, 50 to 70 nm, and it is difficult to discriminate the major axis and the minor axis. It is considered to be caused by shortening of bacterial cell. [The ratio of major axis: minor axis is about 0.9:1.0 to 1.5:1.0, particularly, 1.2:1.0 to 1.5:1.0.]

The bacterial cellulose is characterized by the improvement in Young's modulus which is increased by 30% or more compared with conventional bacterial cellulose obtained in a culture medium not containing cell division inhibitor and organic reducing agent. The Young's modulus of the bacterial cellulose having a major axis of microfibril of 160 to 1000 nm is about 13 to 20 GPa, particularly about 16 to 20 GPa, and the Young's modulus of the bacterial cellulose having a major axis of microfibril of 50 to 70 nm is about 14 to 19 GPa, particularly about 15 to 18.5 GPa. The effect of the improvement in Young's modulus is remarkable in the case of the cellulose obtained by culturing in a culture medium containing a cell deivision inhibitor, particularly, pyridone carboxylic acid based agents. Because major axis of the microfibrils of the bacterial cellulose is considerably lengthened in order to lengthen bacterial cell remarkably. The elongation at rupture of the bacterial cellulose having a major axis of microfibril of 160 to 1000 nm is about 0.9 to 2.1%, particularly about 1.4 to 1.8%, and the elongation at rupture of the bacterial cullulose having a major axis of microfibril of 50 to 70 nm is about 0.9 to 2.0%, particularly 0.9 to 1.5%.

As the chemical components of the bacterial cellulose, there are cullulose, cellulose as a main chain and containing heteropolysaccharides or α, β-, etc., glucans. In the case of heteropolysaccharides, the constituent components, other than cellulose, are hexose, pentose and organic acids, etc., such as mannose, fructose, galactose, xylose, arabinose, ramnose, uronic acid, etc. These polysaccharides may be single substances; alternatively, two or more polysaccharides may coexist.

Microorganisms that produce such bacterial cellulose are not particularly limited, and include, Acetobacter pasteurianus ATCC 23769, FERM BP-4176, Acetobacter aceti, Acetobacter xylinum, Acetobacter rancens, Sarcina ventriculi, Bacterium xyloides and bacteria belonging to the genus Pseudomonas, the genus Agrobacterium, the genus Rhizobium, etc.

*Acetobacter pasteurianus ATCC 23769 was deposited under the terms of the Budapest Treaty on Mar. 17, 1992 under the Accession No. BP-4176 at the National Institute of Bioscience and Human-Technology Agency of Industrial Science and Technology, 1-3, Higashi 1 chome Tsukuba-shi Ibaraki-ken 305 Japan, which is now known as the National Institute of Advanced Industrial Science and Technology, AIST Tsukuba Central 6 1-1, Higashi 1 chome Tsukuba-shi Ibaraki-ken 305 8566 Japan.*

It is important that the culture medium in which cellulose-producing bacterium is cultured contains a cell division inhibitor or an organic reducing agent.

The cell division inhibitor includes chloramphenicol based antibiotics, such as chloramphenicol, protein synthesis inhibitors, such as tetracycline, puromycin and erythromycin, organic compounds having β-lactamase inhibiting ability, such as thienamycin, pyridone carboxylic acid based agents, such as nalidixic acid, promidic acid, pipemidic acid, oxolinaic acid, ofloxacin, enoxacin, and so on. A suitable concentration of the cell division inhibitor is, in the case of chloramphenicol, 0.01 to 5.0 mM, preferably 0.05 to 1.0 mM, more preferably 0.1 to 0.5 mM, and in the case of nalidixic acid, 0.01 to 1.0 mM, preferably 0.05 to 0.3 mM, more preferably 0.1 to 0.2 mM. In a concentration less than the lower end, i.e. 0.01 nM, modification of bacterial cellulose is insufficient, and in a concentration exceeding the upper end, i.e. 5.0 mM or 1.0 mM, growth of bacteria is greatly inhibited.

The organic reducing agent includes dithiothreitol, 2-mercaptoethanol and so on. A suitable concentration of the organic reducing agent is, in the case of dithiothreitol, 0.01 to 5.0 mM, preferably 0.2 to 3.0 mM, more preferably 0.5 to 2.0 mM. In a concentration less than the lower end, modification of bacterial cellulose is insufficient, and in a concentration exceeding the upper end, growth of bacterium is greatly inhibited.

The other components of the culture medium may be similar to a known medium used for culturing the aforementioned bacteria. That is, the culture medium contains a carbon source, a nitrogen source, inorganic salts and, if necessary, organic minor nutrients such as amino acids, vitamins, etc. As the carbon source, glucose, sucrose, maltose, starch hydrolysate, molasses, etc., can be used, but ethanol, acetic acid, nitric acid, etc., may also be used singly or in combination with the above-described sugars. As the nitrogen source, organic or inorganic nitrogen sources such as ammonium salts, e.g. ammonium sulfate, ammonium chloride, ammonium phosphate, etc., nitrates, urea, peptone or the like can be used. Inorganic salts are minor phophates, magnesium salts, calcium salts, iron salts, manganese salts, etc. As organic nutrients amino acids, vitamins, fatty acids, nucleic acids, etc. are used. Furthermore, peptone, casamino acid, yeast extracts, soybean protein hydrolysates, etc., containing these nutrients may be used. When using auxotrophs requiring amino acids, etc., for growth, it is necessary to add required nutrients.

Cultivation method is also not limited, and may be static culture, agitation culture (aeration agitation culture, shaking culture, oscillation culture, air lift type culture) or the like.

The culture conditions may be conventional: for example, at a pH of 3 to 9, preferably 3 to 7, and at a temperature of 1 to 40° C., preferably 25 to 30° C., culture is performed for 1 to 100 days. In the case of static culture, bacterial cullulose is dispersed in the culture solution in the initial stage, and accumulated as a surface layer in a gel form in the later stage.

The gel is withdrawn and washed with water, if necessary. Depending upon the intended use of the gel, the washing water may contain chemicals such as sterilizers, pre-treating agents, etc.

After washing with water, the gel is dried or kneaded with other materials followed by drying. The drying may be carried out by any manner but within the temperature range wherein bacterial cellulose is not decomposed. Since the bacterial cellulose is composed of fine fibers having many hydroxyl groups on their surfaces, it is possible to lose fiber form due to coadhesion of fibers during drying. Accordingly, when bacterial cellulose is used with utilizing fine fiber shape, freeze drying and critical point drying are preferable in order to avoid the coadhesion of fine fibers.

It is preferred that the bacterial cellulose is of structure in which the microfibrils are intertwined, in order to enhance the dynamic strength such as Young's modulus, etc. For this reason, an effective method comprises pressing the gel, harvested from the culture, from the orthogonal direction, squeezing most of the free water off and then drying it. It is appropriate that the squeezing pressure be approximately 1 to 10 kg/cm$^2$. By this press squeezing, the cellulose after drying is orientated along the press squeezing direction. Furthermore, by stretching in one direction while applying pressure, e.g. by performing a rolling operation, the cellulose after drying is orientated also in the rolling direction, in addition to the press squeezing direction. Pressing apparatuses can be appropriately chosen from commercially available machines, On the other hand, it is also effective to macerate the bacterial cellulose, in order to increase the dynamic strength. Maceration may be carried out by using a mechanical shearing force. The bacterial cellulose can easily be macerated with, for example, a rotary macerator, a mixer, etc. It is also effective to conduct the aforesaid press squeezing after maceration.

The bacterial cellulose can be formed into various shapes such as sheet-liked shapes, yarn-like shapes, cloth-like shapes, solid-like shapes, etc.

In the case of molding into a sheet-like form, the bacterial cellulose is, if desired, macerated and then formed into a layer, which is squeezed under pressure, if desired, and then dried. By press squeezing, a planar-orientated sheet is obtained; by further rolling, a sheet not only planar-orientated but also uniaxially orientated can be obtained.

It is desired that the drying of the sheet, macerated and/or press squeezed, are carried out after fixing it to a suitable support. By fixing it on a support, the degree of planar-orientation is further enhanced and a sheet having a large dynamic strength can be obtained. As supports, plates, e.g. glass plates, metal plates, etc., having, for example, a net structure, can be used. Any drying temperature can be used as long as the temperature is within a range where the cellulose is not decomposed. In addition to heat drying, freeze drying can also be used.

The thickness of the sheet depends upon its intended use, but is generally about 1 to 500 microns.

The sheet may contain various additives. For example, by incorporating solutions (aqueous or nonaqueous), emulsion, dispersions, powders, melts, etc. of various polymer materials, one or more of strength, weatherproofness, chemical resistance, water resistance, water repellency, anti-static properties, etc., can be imparted to the sheet, depending upon the properties of the additives. By incorporating metals such as aluminium, copper, iron, zinc, etc., or carbon in a powdery form or fibre form, electroconductivity and thermal conductivity can be increased. Further, by incorporating inorganic materials such as titanium oxide, iron oxides, calcium carbonate, kaolin, bentonite, zeolite, mica, alumina, etc., the heat resistance, insulating properties, etc., can be improved or smoothness can be imparted to the surface, depending upon kind thereof. By incorporating low molecular weight organic materials or adhesives, the strength can be further increased. The sheet may be coloured with colouring agents such as phthalocyanine, azo compounds, indigos, safflowers, etc. For coloration, various paints, dyes and pigments can be used in addition thereto. By incorporating medicines or sterilizers, the sheet can also be utilized as a medical sheet.

These kneadings and additives are incorporated in an appropriate amount not exceeding 97% capable of imparting the desired physical properties. The time of the incorporation is not limited, and they may be incorporated in the bacterial cellulose gel or a micerated product thereof; alternatively, they may be incorporated after press squeezing or after drying. Furthermore, they may be incorporated in the culture medium or culture on some occasions. The method of incorporation may be impregnation, as well as by mixing.

On such a sheet can also be laminated a layer of other material. The laminate can be appropriately chosen depending upon the intended purpose of the sheet. The laminate can also be chosen from the aforesaid kneadings or additives; for example, various polymer materials can be coated onto the sheet to impart waterproofness to the sheet.

In the case of paper, the bacterial cellulose gel is macerated, then subjected to paper making and then drying, whereby paper obtained has an excellent tensile strength, resistance to expansion, etc as well as having a high elasticity and a high strength. The paper is chemically stable and excellent in water absorbance and aid permeability. In this case, ordinary additives, treating agents, etc., used for paper making can be utilized and kneadings and additives can also be appropriately chosen from the aforesaid substances and incorporated into the paper.

The sheet formed of the bacterial cellulose is usable as an acoustic diaphragm having excellent properties.

Other uses are disclosed in U.S. Pat. No. 4,742,164, etc.

EXAMPLES

Example 1

The culture medium used was composed of 50.0 g/l sucrose, 5.0 g/l "Total Amino Acid" (Ajinomoto Co., Inc.), 0.2 g/l phytic acid, 2.4 g/l magnesium sulfate and 1.0 g/l ammonium sulfate (pH 5.0).

Seed culture was carried out by placing 20 ml of the above culture medium in a 100 ml flask with baffle, inoculating Acetobacter pasteurianus FERM BP-4176, and then culturing at 25° C. for 3 days with stirring at 200 rpm. The culture medium was crushed by a blender, and added to a main culture medium having the above composition in a concentration of 2% seed culture.

The main culture was carried out by static culture at 25° C. During the culture, culture solution and bacterial cellulose were withdrawn, and the morphology of bacteria was observed by an optical microscope, an electron microscope and an atomic force microscope.

Six main culture media were used, and nalidixic acid (NA) was added thereto in a concentration of 0.01 mM, 0.05 mM, 0.1 mM, 0.2 mM or 1.0 mM except one medium to which NA was not added.

As a result, production of bacterial cellulose was inhibited with increasing the NA concentration. For example, the shape of the bacterium after cultured in the medium containing 0.1 mM NA and that cultured in the medium not containing NA for 2 days were compared by taking each an optical microscope photograph (×1000). As a result, in the case of 0.1 mM NA, the shape of bacterium was varied and lengthened 2 to 4 times compared with no addition of NA.

The ribbon-shaped microfibrils produced in NA-added media were observed by the electron microscope and the atomic force microscope, and found that the major axes (width) was great, e.g. 170 nm, 340 nm, 430 nm, 590 nm, etc., but the minor axes (thickness) were in the range of [10 to 100 nm, e.g., 25 nm, 30 nm, 60 nm, 90 nm] *1 to 9 nm, e.g., 2.5 nm, 3 nm, 6 nm, 9 nm* etc. On the other hand, the ribbon-shaped microfibrils produced in no NA added medium had a major axis (width) of 82 nm, 107 nm, etc and a minor axis (thickness) in the range of [10 to 100] *1 to 9* nm, and significant variation was not observed compared with NA added medium concerning the minor axis.

Figure 2:
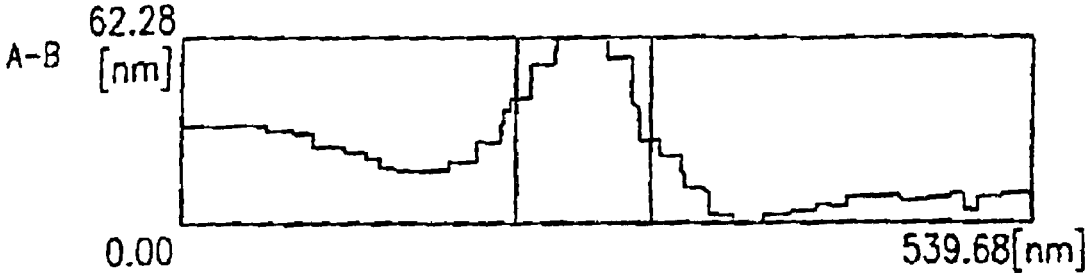
FIG. 2 is a section taken on line A-B of FIG. 1 which was judged to be a minor axis portion.
Figure 3:
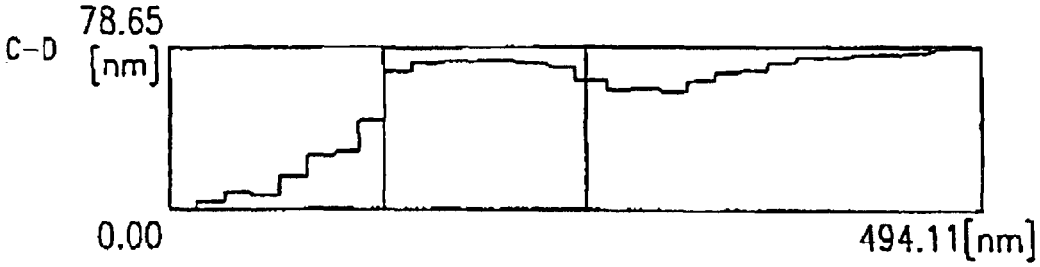
FIG. 3 is a section taken on line C-D of FIG. 1 which was judged to be a major axis.

A part of cellulose gel after culturing 2 days was harvested, and put on a cover glass. The cover glass was allowed to stand at room temperature for 10 to 20 minutes to dry the surface naturally. The cellulose gel was observed by an atomic force microscope ("SPM-9500", Shimazu Seisakusho), and an example is shown in FIGS. 1–3. FIG. 1 is an atomic force microscope photograph of a cellulose-producing bacterium grown in a culture medium not containing cell division inhibitor and organic reducing agent which is secreting bacterial cellulose. An operation seeks the narrowest part and the widest part of a cellulose fiber produced from the bacterium, and lines for image analysis are drawn at those parts in the direction perpendicular to the fiber lengthwise direction on the image displayed on a display of a computer connected to the atomic force microscope, and the shape (section) in the direction perpendicular to the fiber lengthwise direction is displayed (FIGS. 2,3). Then, the operator operates the computer to display each length. The minor axis indicated by A-B line was ca. 86 nm, and the major axis indicated by C-D line was ca. 123 nm.

After culturing for 40 days, the bacterial cellulose gel was taken out, and washed with running water, alkali, and then running water, successively. The washed bacterial cellulose was pressed into sheet and properties were measured as to 0.1 mM NA, 0.2 mM and no NA.

Each bacterial cellulose sheet was punched into dumbbell pieces of JIS standard No.3 having a width of 1.0 cm and a length of 2.0 cm, and used as test pieces. After measuring the thickness of each test pieces, and its strength was measured by a tensile tester "Tensilon RTM-600 Type" (Orintec Corp.) with drawing at a rate of 20 mm/min, the results are shown in Table 1.

TABLE 1

| NA (mM) | Thickness (μm) | Mean Thickness (μm) | Young's Modulus (GPa) | Mean Elastic Modulus (GPa) | Elongation at Rupture (%) | Mean Elongation at Rupture (%) |
|---|---|---|---|---|---|---|
| 0.10 | 33 | 32 | 19.4 | 19.4 | 1.51 | 1.79 |
| | 35 | | 19.7 | | 1.90 | |
| | 31 | | 19.5 | | 2.02 | |
| | 29 | | 19.2 | | 1.72 | |
| 0.20 | 31 | 34 | 16.4 | 16.1 | 1.78 | 1.88 |
| | 35 | | 18.2 | | 2.12 | |
| | 34 | | 13.9 | | 2.03 | |
| | 35 | | 15.8 | | 1.58 | |
| 0 | 25 | 38 | 11.8 | 12.4 | 1.82 | 1.80 |
| | 44 | | 11.3 | | 2.22 | |
| | 54 | | 14.1 | | 1.53 | |
| | 32 | | 12.3 | | 1.62 | |

As shown in Table 1, the sheets obtained by culturing in 0.1 mM NA medium and in 0.2 mM NA medium varied in their properties, and Young's modulus was improved compared with the sheet obtained by culturing in no NA medium.

Example 2

Acetobacter pasteurianus FERM BP-4176 was cultured in static culture, and the culture solution and bacterial cellulose were withdrawn, and the shape of bacteria was observed by the optical microscope, the electron microscope and the atomic force microscope, similar to Example 1, except that chloramphenicol was used instead of nalidixic acid.

That is, six main culture media having the aforementioned composition were used, and chloramphenicol (CP) was added thereto in a concentration of 0.1 mM, 0.2 mM, 0.3 mM, 0.5 mM or 1.0 mM except one medium to which CP was not added.

As a result, the length of the cellulose-producing bacterium increased with increasing the CP concentration up to 8 to 12 times as long as the bacteria cultured in no CP medium.

Figure 4:
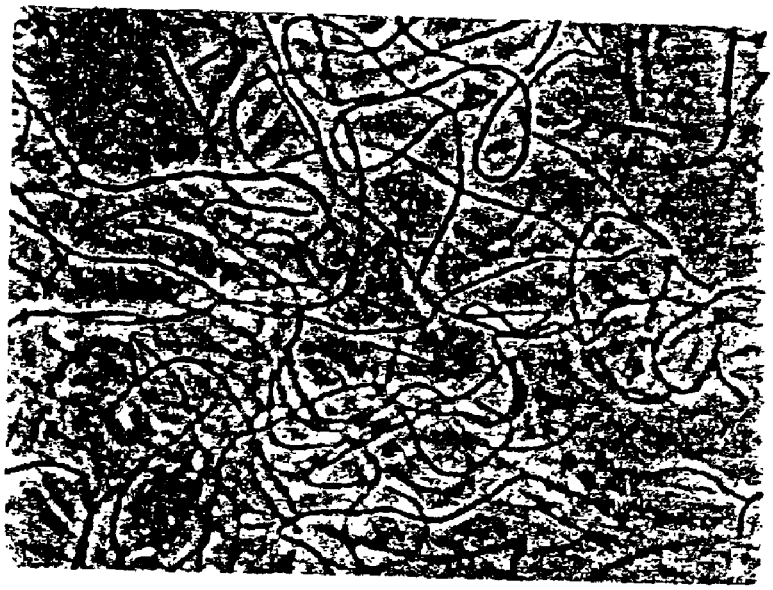
FIG. 4 is a photograph of an optical microscope (×1000) showing a shaped of a cellulose-producing bacterium which was cultured in a 0.3 mM chloramphenol-added culture medium.
Figure 5:
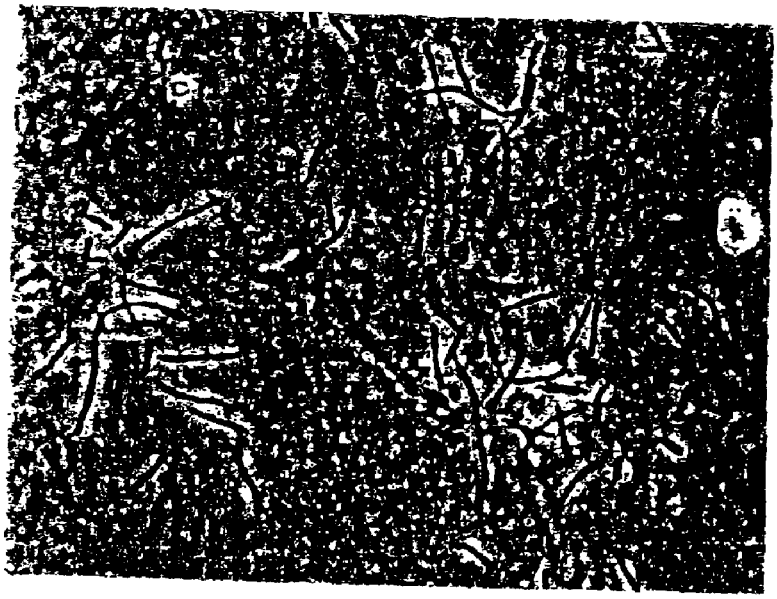
FIG. 5 is a photograph of an optical microscope (×1000) showing a shaped of a cellulose-producing bacterium which was cultured in a culture medium to which chloramphenicol was not added.
Figure 6:
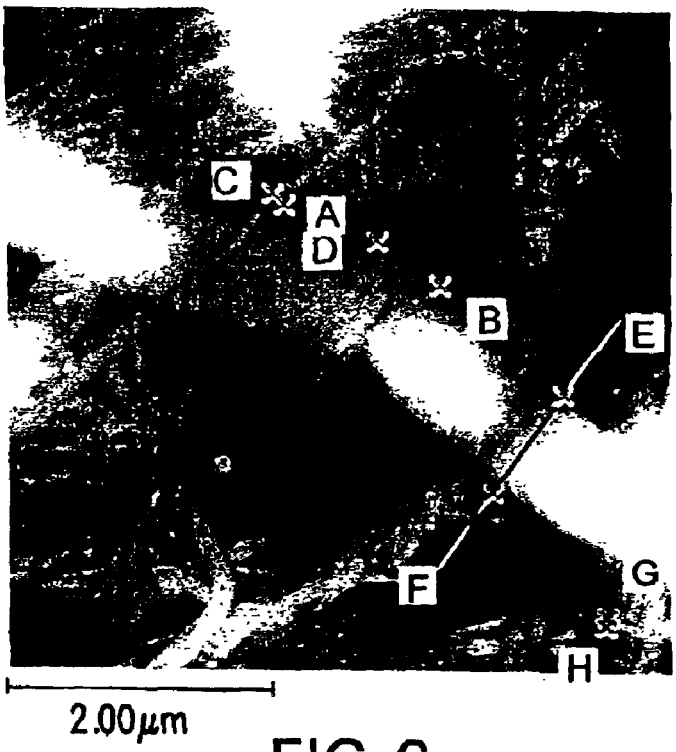
FIG. 6 is a photograph of an atomic force microscope showing a shaped of cellulose fiber and a cellulose-producing bacterium which was cultured in a 0.3 mM chloramphenicol-added culture medium.

As an example, the shape of bacterium cultured in the 0.3 mM CP medium for 2 days taken by the optical microscope (×1000), and shown in FIG. 4, and that cultured in no CP medium for 2 days is shown in FIG. 5.

The CP ribbon-shaped microfibrils produced in NA-added media were observed by the electron microscope and the atomic force microscope, and found that the major axes (width) was great, e.g. 160 nm, 330 nm, 450 nm, 570 nm, 690 nm, etc., but the minor axes (thickness) were in the range of [10 to 100] *1 to 9* nm. On the other hand, the ribbon-shaped microfibrils produced in no CF added medium had a major axis (width) of 82 nm, 107 nm, etc and a minor axis (thickness) in the range of 10 to 100 nm, and significant variation was not observed compared with CP added medium concerning the minor axis.

After culturing 40 days, the bacterial cellulose produced was made into a sheet, and properties of the sheets obtained from 0.2 mM CP, 0.3 mM CP or no CP were measured, similar to example 1. The results are shown in Table 2.

TABLE 2

| CP (mM) | Thickness (μm) | Mean Thickness (μm) | Young's Modulus (GPa) | Mean Elastic Modulus (GPa) | Elongation at Rupture (%) | Mean Elongation at Rupture (%) |
|---|---|---|---|---|---|---|
| 0.20 | 35 | 36 | 18.2 | 19.3 | 1.63 | 1.29 |
| | 37 | | 20.2 | | 1.26 | |
| | 35 | | 19.4 | | 1.03 | |
| | 36 | | 19.6 | | 1.22 | |
| 0.30 | 34 | 35 | 13.4 | 16.5 | 1.93 | 1.40 |
| | 37 | | 17.8 | | 1.42 | |
| | 35 | | 14.5 | | 1.28 | |
| | 34 | | 18.2 | | 0.98 | |
| 0 | 25 | 38 | 11.8 | 12.4 | 1.82 | 1.80 |
| | 44 | | 11.3 | | 2.22 | |
| | 51 | | 14.1 | | 1.53 | |
| | 32 | | 12.3 | | 1.62 | |

As shown in Table 2, the sheet obtained by culturing in 0.2 mM 0.3 mM CP medium varied in its properties, and Young 's modulus was improved compared with the sheet obtained by culturing in no CP medium.

Example 3

Acetobacter pasteurianus FERM BP-4176 was cultured in static culture, and the culture solution and bacterial cellulose were withdrawn, and the form of bacteria was observed by the optical microscope, the electron microscope and the atomic force microscope, similar to Example 1, except that chloramphenicol was used instead of nalidixic acid.

That is, four main culture media having the aforementioned composition were used, and dithiothreitol (DTT) was added thereto in a concentration of 0.5 mM, 1.0 mM or 2.0 mM except one medium to which DTT was not added.

As a result, the length of the cellulose-producing bacterium decreased with increasing the DTT concentration.

Figure 7:
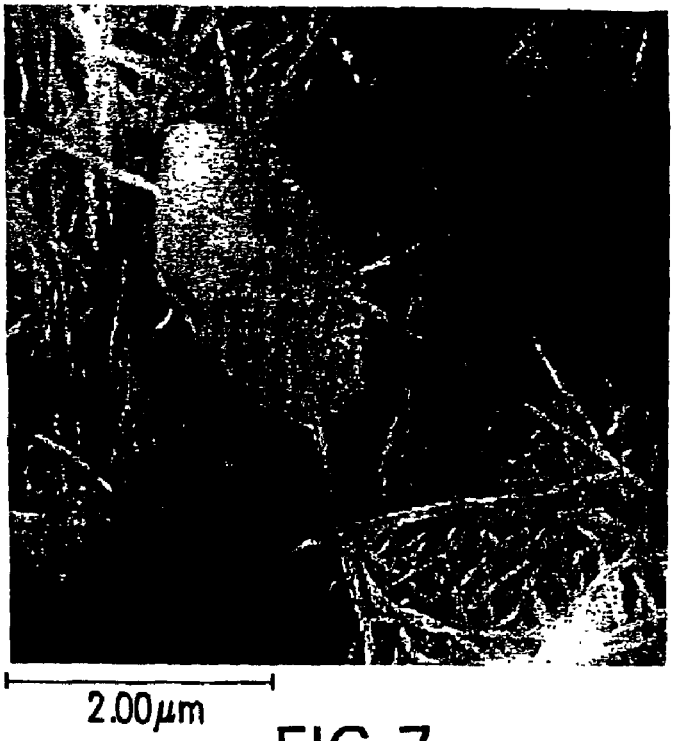
FIG. 7 is a photograph of an atomic force microscope showing a shaped of cellulose fiber and a cellulose-producing bacterium which was cultured in a 1.0 mM dithiothreitol-added culture medium.

As an example, the shape of bacterium cultured in the 1.0 mM DTT medium for 2 days taken by the optical microscope, and shown in FIG. 7. As can be seen from the photograph, the length of the bacterium cultured in 1.0 mM DTT medium wat shortened to ⅓ to ½ of the bacteria cultured in no DTT medium.

The DTT ribbon-shaped microfibrils produced in NA-added media were observed by the electron microscope and the atomic force microscope, and found that the major axes (width) was small, e.g. 56 nm, 57 nm, 70 nm, etc., but the minor axes (thickness) were in the range of [10 to 100] *1 to 9* nm. On the other hand, the ribbon-shaped microfibrils produced in no DTT added medium had a major axis (width) of 82 nm, 107 nm, etc and a minor axis (thickness) in the range of [10 to 100] *1 to 9* nm, and significant variation was not observed compared with DTT added medium concerning the minor axis.

After culturing 40 days, the bacterial cellulose produced made into a sheet, and properties of the sheets obtained mM DTT, 0.5 mM DTT or no DTT were measured similar to Example 1. The results are shown in Table 3

TABLE 3

| DTT (mM) | Thickness (μm) | Mean Thickness (μm) | Young's Modulus (GPa) | Mean Elastic Modulus (GPa) | Elongation at Rupture (%) | Mean Elongation at Rupture (%) |
|---|---|---|---|---|---|---|
| 0.50 | 38 | 38 | 18.5 | 17.8 | 1.00 | 1.32 |
| | 37 | | 17.1 | | 1.10 | |
| | 40 | | 18.8 | | 1.87 | |
| | 36 | | 16.9 | | 1.32 | |
| 1.0 | 54 | 45 | 15.4 | 16.2 | 0.97 | 1.70 |
| | 36 | | 15.8 | | 2.10 | |
| | 37 | | 18.5 | | 2.07 | |
| | 52 | | 15.1 | | 1.67 | |
| 0 | 25 | 38 | 11.8 | 12.4 | 1.82 | 1.80 |
| | 44 | | 11.3 | | 2.22 | |
| | 51 | | 14.1 | | 1.53 | |
| | 32 | | 12.3 | | 1.62 | |

As shown in Table 3, the sheet obtained by culturing in 0.5 mM DTT, 1.0 mM DTT medium varied in its properties, and Young's modulus was important compared with the sheet obtained by culuring in no DTT medium.

Example 4

Acetobacter pasteurianus FERM BP-4176 was cultured in agitation culture at 180 rpm instead of static culture, and the culture solution and bacterial cellulose were withdrawn, and the shape of bacteria was observed by the optical microscope, the electro microscope and the atomic force microscope, similar to Example 1.

That is, four main culture media having the aforementioned composition were used, and nalidixic acid (NA) was added thereto in a concentration of 0.10 mM, or 0.20 mM, except one medium to which NA was not added.

As a result, the length of the cellulose-producing bacteria increased. The ribbon-shaped microfibrils produced in NA-added media were observed by the electron microscope and the atomic force microscope, and found that the major axes (width) was great, e.g. 170 nm, 250 nm, etc., but variation in the minor axes was not observed.

After culturing 14 days, the bacterial cellulose produced was made into a sheet, and Young's modulus of the sheets were measured, similar to Example 1.

As a result, the sheets obtained by culturing in 0.1 mM NA medium and in 0.2 mM NA medium varied in their properties, and Young's modulus was improved compared with the sheet obtained by culturing in no NA medium.

What is claimed is:

[1. An isolated and purified bacterial cellulose comprising microfibrils having a thickness of 10 to 100 nm and a width of 250 to 1000 nM.]

[2. The bacterial cellulose of claim 1, which has a width of 250 to 700 nm.]

[3. The bacterial cellulose of claim 1, which has a width of 250 to 600 nm.]

[4. The bacterial cellulose of claim 1, which has a width of 170 to 1000 nm.]

[5. The bacterial cellulose of claim 1, which has a width of 250 to 700 nm.]

[6. The bacterial cellulose of claim 1, which has a width of 250 to 600 nm.]

[7. The bacterial cellulose of claim 1, wherein the microfibrils are ribbon-shaped.]

[8. A method of producing the bacterial cellulose of claim 1, which comprises culturing cellulose-producing bacteria which produce the bacterial cellulose extracellularly in a culture medium containing a cell division inhibitor, and recovering the bacterial cellulose produced in the culture medium.]

[9. The method of claim 8, wherein the cell division inhibitor is selected from the group consisting of chloramphenicol, a protein synthesis inhibitor, an organic compound having β-lactamase inhibiting ability, nalidixic acid, promidic acid, pipemidic acid, oxolinaic acid, ofloxacin and enoxacin.]

[10. The method of claim 9, wherein the protein synthesis inhibitor is selected from the group consisting of tetracycline, puromycin and erythromycin.]

[11. The method of claim 9, wherein the organic compound having β-lactamase inhibiting ability is thienamycin.]

[12. The method of claim 8, wherein the concentration of the cell division inhibitor in the culture medium is 0.01 to 5 mM.]

[13. The method of claim 8, wherein the bacteria are Acetobacter.]

[14. The method of claim 8, wherein the bacteria are Acetobacter pasteurianus FERM BP-4176.]

[15. The bacterial cellulose of claim 1, which has a width of 430 to 1000 nm.]

[16. The bacterial cellulose of claim 1, which has a width of 590 to 1000 nm.]

[17. The bacterial cellulose of claim 1, which has a Young's modulus of 13 to 20 GPa.]

[18. The bacterial cellulose of claim 1, which has a Young's modulus of 16 to 20 GPa.]

[19. The bacterial cellulose of claim 1, which has a width of 340 to 1000 nm.]

[20. The bacterial cellulose of claim 1, which has a width of 340 to 700 nm.]

[21. The bacterial cellulose of claim 1, which has a width of 340 to 600 nm.]

*22. A bacterial cellulose comprising microfibrils having a thickness of 1 to 9 nm and a width of 250 to 1000 nm.*

*23. The bacterial cellulose of claim 22, wherein the microfibrils have a width of 250 to 700 nm.*

*24. The bacterial cellulose of claim 22, wherein the microfibrils have a width of 250 to 600 nm.*

*25. The bacterial cellulose of claim 22, wherein the microfibrils are ribbon-shaped.*

*26. A method of producing the bacterial cellulose of claim 22, which comprises culturing cellulose-producing bacteria which produce the bacterial cellulose extracellularly in a culture medium containing a cell division inhibitor, and recovering the bacterial cellulose produced in the culture medium.*

*27. The method of claim 26, wherein the cell division inhibitor is selected from the group consisting of chloramphenicol, a protein synthesis inhibitor, an organic compound having β-lactamase inhibiting ability, nalidixic acid, promidic acid, pipemidic acid, oxolinaic acid, ofloxacin and enoxacin.*

*28. The method of claim 27, wherein the protein synthesis inhibitor is selected from the group consisting of tetracycline, puromycin and erythromycin.*

*29. The method of claim 27, wherein the organic compound having β-lactamase inhibiting ability is thienamycin.*

*30. The method of claim 26, wherein the concentration of the cell division inhibitor in the culture medium is 0.01 to 5 mM.*

*31. The method of claim 26, wherein the bacteria are Acetobacter.*

*32. The method of claim 26, wherein the bacteria are Acetobacter pasteurianus FERM BP-4176.*

*33. The bacterial cellulose of claim 22, wherein the microfibrils have a width of 430 to 1000 nm.*

*34. The bacterial cellulose of claim 22, wherein the microfibrils have a width of 590 to 1000 nm.*

*35. The bacterial cellulose of claim 22, wherein the microfibrils have a Young's modulus of about 13 to 20 GPa.*

*36. The bacterial cellulose of claim 22, wherein the microfibrils have a Young's modulus of about 16 to 20 Gpa.*

*37. The bacterial cellulose of claim 22, wherein the microfibrils have a width of 340 to 1000 nm.*

*38. The bacterial cellulose of claim 22, wherein the microfibrils have a width of 340 to 700 nm.*

*39. The bacterial cellulose of claim 22, wherein the microfibrils have a width of 340 to 600 nm.*

*40. The bacterial cellulose of claim 22, wherein the microfibrils have a thickness of 2.5, 3, 6, or 9 nm.*

*41. The bacterial cellulose of claim 22, wherein the ratio of the major axis to the minor axis of the microfibrils is about 28:1.0 to 1000:1.0.*

*42. The bacterial cellulose of claim 22, wherein the ratio of the major axis to the minor axis of the microfibrils is about 28:1.0 to 280:1.0.*

*43. The bacterial cellulose of claim 22, which is isolated and purified.*

*44. A bacterial cellulose produced by Acetobacter pasteurianus FERM BP-4176 which comprises microfibrils having a thickness of 1 to 9 nm and a width of 250 to 1000 nm.*

*45. The bacterial cellulose of claim 44, wherein the microfibrils have a width of 250 to 700 nm.*

*46. The bacterial cellulose of claim 44, wherein the microfibrils have a width of 250 to 600 nm.*

*47. The bacterial cellulose of claim 44, wherein the microfibrils have a width of 430 to 1000 nm.*

*48. The bacterial cellulose of claim 44, wherein the microfibrils have a width of 590 to 1000 nm.*

*49. The bacterial cellulose of claim 44, wherein the microfibrils have a width of 340 to 1000 nm.*

*50. The bacterial cellulose of claim 44, wherein the microfibrils have a width of 340 to 700 nm.*

*51. The bacterial cellulose of claim 44, wherein the microfibrils have a width of 340 to 600 nm.*

*52. The bacterial cellulose of claim 44, wherein the microfibrils have a Young's modulus of about 13 to 20 GPa.*

*53. The bacterial cellulose of claim 44, wherein the microfibrils have a Young's modulus of about 16 to 20 Gpa.*

*54. The bacterial cellulose of claim 44, wherein the ratio of the major axis to the minor axis of the microfibrils is about 28:1.0 to 1000:1.0.*

*55. The bacterial cellulose of claim 44, wherein the ratio of the major axis to the minor axis of the microfibrils is about 28:1.0 to 280:1.0.*

*56. The bacterial cellulose of claim 44, wherein the microfibrils are ribbon-shaped.*

*57. A method of producing the bacterial cellulose of claim 44, which comprises culturing cellulose-producing bacteria which produce the bacterial cellulose extracellularly in a culture medium containing a cell division inhibitor, and recovering the bacterial cellulose produced in the culture medium.*

*58. The method of claim 57, wherein the cell division inhibitor is selected from the group consisting of chloramphenicol, a protein synthesis inhibitor, an organic compound having β-lactamase inhibiting ability, nalidixic acid, promidic acid, pipemidic acid, oxolinaic acid, ofloxacin and enoxacin.*

*59. The method of claim 58, wherein the protein synthesis inhibitor is selected from the group consisting of tetracycline, puromycin and erythromycin.*

*60. The method of claim 58, wherein the organic compound having β-lactamase inhibiting ability is thienamycin.*

*61. The method of claim 57, wherein the concentration of the cell division inhibitor in the culture medium is 0.01 to 5 mM.*

*62. The method of claim 57, wherein the bacteria are Acetobacter.*

*63. The method of claim 57, wherein the bacteria are Acetobacter pasteurianus FERM BP-4176.*

* * * * *